United States Patent

Edmonds

[11] Patent Number: 4,722,226
[45] Date of Patent: Feb. 2, 1988

[54] ACOUSTIC MONITOR FOR ROTARY ELECTRICAL MACHINERY

[75] Inventor: James S. Edmonds, Mountain View, Calif.

[73] Assignee: Electric Power Research Institute, Palo Alto, Calif.

[21] Appl. No.: 850,229

[22] Filed: Apr. 10, 1986

[51] Int. Cl.⁴ .............................................. G01N 29/04
[52] U.S. Cl. ......................................... 73/660; 73/593
[58] Field of Search ........................... 73/660, 593, 587

[56] References Cited

U.S. PATENT DOCUMENTS

| 2,204,425 | 6/1940 | Mershon | 73/660 |
| 4,004,464 | 1/1977 | Himmler | 73/660 |
| 4,518,917 | 5/1985 | Oates et al. | 73/660 |
| 4,573,358 | 3/1986 | Luongo | 73/660 |

Primary Examiner—Stewart J. Levy
Assistant Examiner—Louis M. Arana
Attorney, Agent, or Firm—Flehr, Hohbach, Test, Albritton & Herbert

[57] ABSTRACT

Loose field windings in a rotating electrical machine are detected by sensing acoustic waves created by stator bars and stator wedges. A sensor is mounted on the rotor which responds to sensed acoustic waves by generating an electrical signal. The signal is suitably conditioned and transmitted by telemetry means to a computer for processing.

5 Claims, 5 Drawing Figures

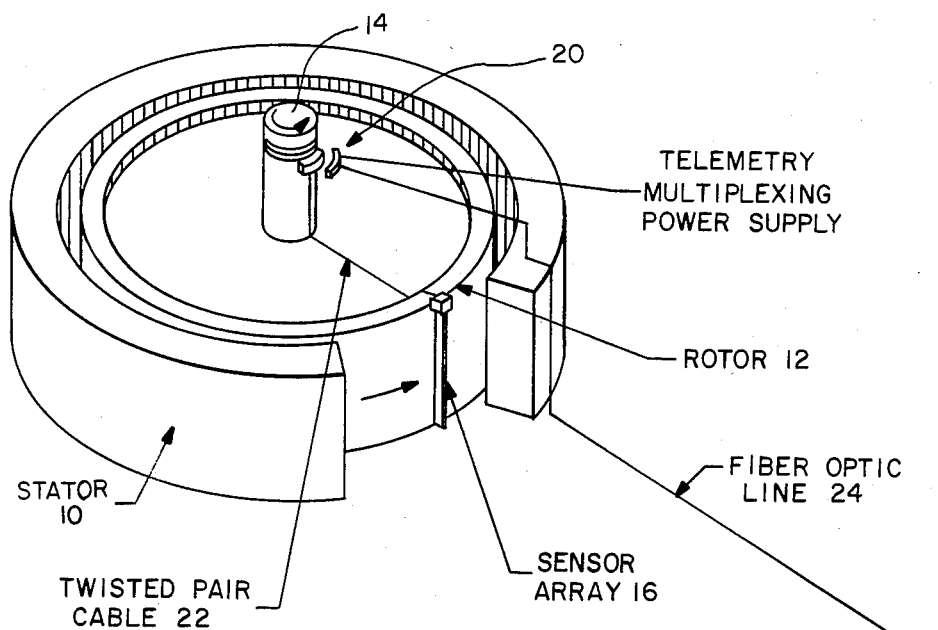
FIG.—1
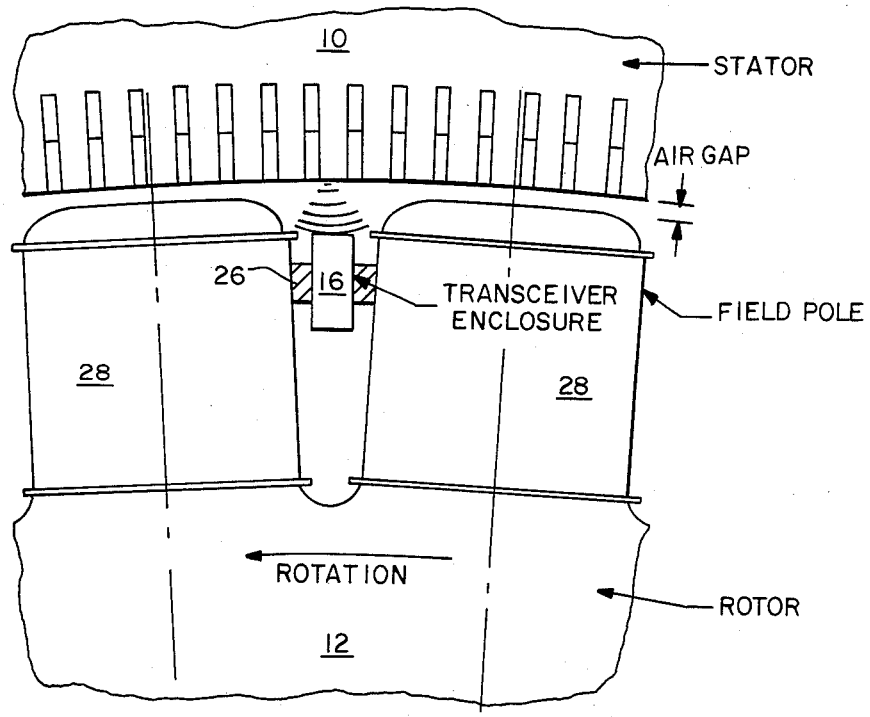
FIG.—2

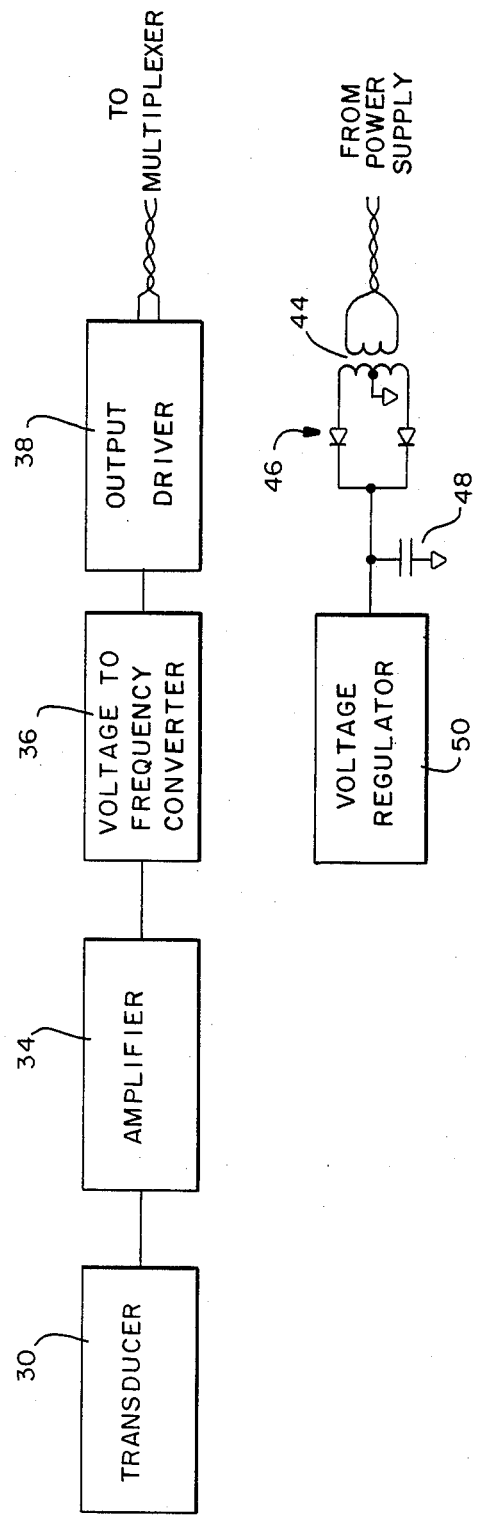
FIG.—3

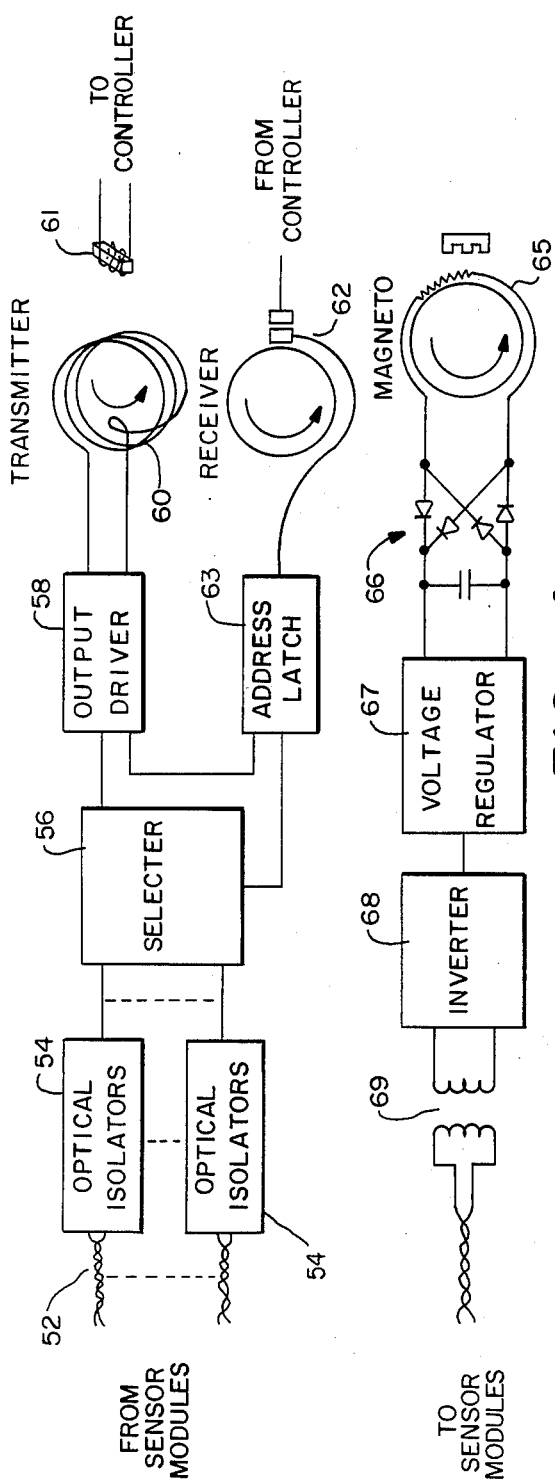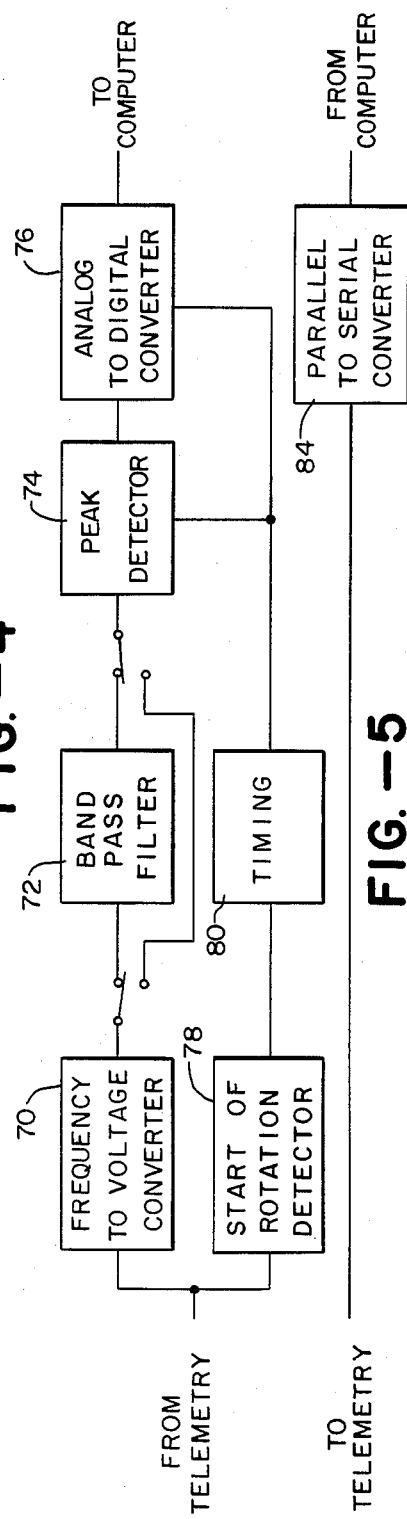

ACOUSTIC MONITOR FOR ROTARY ELECTRICAL MACHINERY

BACKGROUND OF THE INVENTION

This patent application is related to copending application Ser. No. 850,234, filed Apr. 10, 1986 for DYNAMIC AIR GAP MEASURING DEVICE FOR USE WITH ROTATING ELECTRICAL MACHINERY filed concurrently herewith.

This invention relates generally to rotating electrical machinery, and more particularly the invention relates to the detection of loose coils in the stator of such machinery.

In the hydroelectric generator, voltage and current are induced in windings of the stator due to the rotation of the rotor and rotor windings within the stator. With the advent of epoxy insulation systems, the physical characteristics of generator stator windings changed. The former asphaltic insulation systems would swell over a period of time at temperatures reached during normal operation. This swelling locks the stator bar into the stator slot, thereby preventing relative movement caused by the high interacting magnetic forces. Epoxy insulation does not expand with time and temperature but instead tends to shrink slightly as the curing process continues. For this reason, it has been difficult to install a winding in a generator that will remain completely tight over a long period of time; this is particularly true for hydroelectric generators. As the stator winding components begin to loosen, the alternating magnetic forces cause the stator bars and stator wedges to "chatter" against the sides of the stator slot.

No technique has been available for determining when components in a hydroelectric generator stator become loose. Even though this is a major problem for the utility industry, the industry has had to rely on periodic inspections to locate the effects and damage caused by this phenomenon, thus a device and a method are needed to be able to detect this looseness before the insulation is worn off and the machine fails from an electrical short circuit.

The present invention is directed to detecting field winding looseness by acoustically monitoring noise or "chatter" created by the stator bars and stator wedges. On salient pole generators, there is generally sufficient room between pole pieces on the rotor to mount an acoustic monitor for the purpose of continuously monitoring the stator windings. If any components of the stator or winding are loose, the hammering of these components will tend to create acoustic energy at a frequency that is twice the rated frequency of the generator (e.g., 120 Hz for a 60 Hz generator). The acoustic energy is picked up by microphones that would be developed especially for this application and environment. The acoustic transducer must be immune to external electromagnetic radiation.

In order to cover a wide range of acoustical frequencies, the monitor scans a range from DC up to about 10 KHz. The source of the sound created by loose components is determined by a specific timing reference associated with the rotation of the rotor and the known doppler shift in frequency as the rotor-mounted sensor approaches the sound source and as the sensor departs the sound source.

Briefly, an acoustic monitor in accordance with the invention comprises an acoustic transducer mounted on the rotor and oriented to receive acoustic signals from the stator windings. The transducer converts the acoustic signals to electrical signals which can be processed to identify loose windings.

In a preferred embodiment the electrical signals from one or more rotor mounted monitors are amplified and then applied to a voltage to frequency converter for conversion to pulses for transmission. The pulses are applied to a suitable output driver such as an FM modulator, and the output of the driver is then applied to an RF transmitter on the rotor for coupling to a receiver. The receiver transmits the signal to computer means for analysis. Control signals from the computer means are coupled to the rotor for sensor control through a multiplexer in the case of a plurality of monitors.

The invention and objects and features thereof will be more readily apparent from the following detailed description and appended claims.

BRIEF DESCRIPTION OF THE DRAWINGS

FIG. 1 is a perspective view partially in section of an electric generator including an acoustic monitor in accordance with one embodiment of the invention.

FIG. 2 is a section view of a portion of the stator and rotor of the generator of FIG. 1 illustrating the positioning of the acoustic monitoring apparatus therein.

FIG. 3 is a functional block diagram of one embodiment of the acoustic monitor.

FIG. 4 is a functional block diagram of telemetry apparatus in the system of FIG. 1.

FIG. 5 is a functional block diagram of computer interface circuitry for use in the system of FIG. 1.

DETAILED DESCRIPTION OF THE SPECIFIC EMBODIMENTS

FIG. 1 is a perspective view partially in section of an electrical generator including acoustic monitoring apparatus in accordance with the invention. The generator includes a generally cylindrical stator 10 in which a rotor 12 rotates on a shaft 14. The stator is shown partially in section to illustrate a sensor array 16 of the acoustic monitor. In this embodiment the acoustic monitor is mounted on the rotor.

The sensor array 16 is electrically and optically coupled to a central computer 18 through an electrical and optical telemetry coupler shown generally at 20. One part of the coupler 20 is mounted to shaft 14 and is electrically connected to the sensor array 16 by means of a twisted pair cable 22. The other portion of the coupler 20 is mounted to the stator structure and is periodically aligned with the rotor mounted portion of the coupler as the shaft rotates. The stator portion of coupler 20 is connected to the computer 18 through a fiber optic link 24.

FIG. 2 is a section view of a portion of the stator 10 and the rotor 12 and illustrates the positioning of the sensor array 16 between field pole pieces 28 of the rotor. The housing for the sensor array 16 is preferably a machined aluminum container having a rectangular cross section, and the aluminum housing is mounted to the pole pieces 28 by suitable means such as a stainless steel support frame of bridge 26.

The acoustic wave sensor of the monitor is preferably an acoustic transducer such as a microphone. FIG. 3 is a functional block diagram on one embodiment in which an acoustic transducer 30 is provided to receive acoustic waves. Transducer 30 generates an electrical signal in response to the acoustic waves, and the electrical signal is amplified in amplifier 34 and applied through voltage to frequency converter 36 to an output driver 38. The output driver 38 converts the pulsed output from converter 36 to a low impedance signal without noise contamination and transmits the signal through the twisted wire pair 40 to the telemetry coupler, as shown in FIG. 4. Power for the circuitry on the rotor is provided through a 20 Khz square wave transmitted to transformer 44, converted to dc by full wave rectifier 46 and capacitor 48, and then applied to regulator 50. The power supply and the telemetry employed in the described system is known in the prior art.

The signals from the output driver 38 are communicated to the computer through any suitable telemetry system, such as the system shown in FIG. 4. With reference to FIG. 4, the signals from the sensor modules are applied through lines 52, optical isolator 54 and MUX selector 56 to an output FN.M driver 58. FM driver 58 continuously drives a transmitting coil 60. Coil 60 is coupled to a ferrite antenna 61 which generates a signal that is amplified and converted to light pulses. The light pulses then are sent to the controller computer through a fiber optic cable. Optical signals from the controller are transmitted once per revolution through a coupler 62 to an address latch 63 for sensor selection. The transmitted code is stored in address latch 63 and is used to determine which sensor module output to send, and the reception of the code will cause a long pulse to be transmitted by the output driver. This long pulse is detected by the system computer and used to indicate when the rotor is starting a new revolution with another sensor sending data. Power to the sensors is provided using known techniques such as the use of magneto 65, full wave rectifier 66, regulator 67, inverter 68, and transformer 69.

FIG. 5 is a functional block diagram of the controller interface. The sensor output voltages are restored from optical transmission data by a frequency voltage converter 70 and then routed through a digitally controlled bandpass filter 72. The bandpassed signals are stored by the detector 74 and converted to a computer readable number by analog-to-digital converter 76. The long start of rotation pulse from the rotor telemetry is detected at 78 and used to synchronize a phase locked loop timing circuit 80. Timing circuit 80 in turn controls the analog-to-digital converter and provides reset pulses to the peak detector 74. The parallel data codes from the computer are converted to serial code by converter 84, and the bits of the serial code are then transmitted through a fiber optic cable to the optical transmitter at the generator and then converted back to parallel bits at the transmitter.

The acoustic monitoring device is particularly useful with large rotating electrical machinery as described. However, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In rotating electrical machinery including a stator and a rotor mounted for rotation in the stator, a method of detecting loose stator windings comprising the steps of
    mounting an acoustic sensor on said rotor and positioned to receive acoustic waves from said stator,
    generating electrical signals in response to acoustic waves from said stator, and
    analyzing said electrical signals to determine acoustic noise created by a loose winding.

2. The method as defined by claim 1 wherein said step of analyzing said electrical signals includes providing computer means and transmitting said electrical signals to said computer means by telemetry means.

3. The method as defined by claim 1 and further including the step of generating a mark signal at the beginning of each revolution of said rotor for stator position identification.

4. An acoustic monitor for detecting stator coil movement in a rotary electrical machine having a stator and a rotor, said monitor comprising
    an acoustic sensor mounted to said rotor and oriented to receive acoustic waves from said stator and generate an electrical signal in response thereto
    signal amplification and drive circuitry for receiving, amplifying and converting said electrical signal for transmission,
    telemetry means for transmitting the electrical signal from said signal amplification and drive circuitry, and
    computer means for receiving the transmitted signal and identifying acoustic noise from a moving stator coil.

5. The acoustic monitor as defined by claim 4 and further including a plurality of sensors and signal amplification and drive circuitry, multiplexer means for selectively applying signals to said telemetry means, and control means responsive to said computer means for controlling said multiplexer means.

* * * * *